United States Patent
Arndt et al.

(10) Patent No.: US 6,512,956 B2
(45) Date of Patent: Jan. 28, 2003

(54) METHOD OF CONSTRUCTING A MICROWAVE ANTENNA

(75) Inventors: G. Dickey Arndt, Friendswood, TX (US); James Carl, Houston, TX (US); Phong Ngo, Friendswood, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 71 days.

(21) Appl. No.: 09/746,541

(22) Filed: Dec. 18, 2000

(65) Prior Publication Data

US 2001/0020180 A1 Sep. 6, 2001

Related U.S. Application Data

(60) Division of application No. 09/511,961, filed on Feb. 23, 2000, which is a continuation-in-part of application No. 09/154,989, filed on Sep. 17, 1998, now Pat. No. 6,134,476, which is a continuation-in-part of application No. 09/162,457, filed on Sep. 16, 1998, now abandoned, which is a continuation-in-part of application No. 09/154,622, filed on Sep. 16, 1998, now Pat. No. 6,175,768, which is a continuation-in-part of application No. 08/641,045, filed on Apr. 17, 1996, now Pat. No. 5,904,709.

(51) Int. Cl.$^7$ .................................................. A61F 2/00
(52) U.S. Cl. ........................ 607/101; 607/156; 607/154
(58) Field of Search ................................. 607/100, 101, 607/102, 115, 116, 122, 123, 154, 156; 606/33, 35, 42, 23, 49, 50

(56) References Cited

U.S. PATENT DOCUMENTS

| | | | |
|---|---|---|---|
| 4,967,765 A | 11/1990 | Turner et al. | |
| 5,312,392 A | 5/1994 | Hofstetter et al. | |
| 5,366,490 A | 11/1994 | Edwards et al. | |
| 5,413,588 A | 5/1995 | Rudie et al. | |
| 5,464,437 A | 11/1995 | Reid et al. | |
| 5,496,271 A | * 3/1996 | Burton et al. | 604/101.05 |
| 5,509,929 A | 4/1996 | Hascoet et al. | |
| 5,575,811 A | 11/1996 | Reid et al. | |
| 5,599,294 A | 2/1997 | Edwards et al. | |
| 5,620,480 A | 4/1997 | Rudie | |
| 5,643,335 A | 7/1997 | Reid et al. | |
| 5,720,718 A | 2/1998 | Rosen et al. | |
| 5,800,378 A | 9/1998 | Edwards et al. | |
| 5,800,486 A | 9/1998 | Thome et al. | |
| 5,843,026 A | 12/1998 | Edwards et al. | |
| 5,843,144 A | 12/1998 | Rudie et al. | |
| 5,904,709 A | 5/1999 | Arndt et al. | |
| 6,016,811 A | * 1/2000 | Knopp et al. | 128/898 |
| 6,033,401 A | * 3/2000 | Edwards et al. | 606/214 |
| 6,251,128 B1 | * 6/2001 | Knopp et al. | 607/100 |
| 6,350,276 B1 | * 2/2002 | Knowlton | 607/101 |

\* cited by examiner

*Primary Examiner*—Linda C. M. Dvorak
*Assistant Examiner*—Kenneth Schopfer
(74) *Attorney, Agent, or Firm*—Hardie R. Barr; Theodore U. Ro

(57) ABSTRACT

A method, simulation, and apparatus are provided that are highly suitable for treatment of benign prostatic hyperplasia (BPH). A catheter is disclosed that includes a small diameter disk loaded monopole antenna surrounded by fusion material having a high heat of fusion and a melting point preferably at or near body temperature. Microwaves from the antenna heat prostatic tissue to promote necrosing of the prostatic tissue that relieves the pressure of the prostatic tissue against the urethra as the body reabsorbs the necrosed or dead tissue. The fusion material keeps the urethra cool by means of the heat of fusion of the fusion material. This prevents damage to the urethra while the prostatic tissue is necrosed. A computer simulation is provided that can be used to predict the resulting temperature profile produced in the prostatic tissue. By changing the various control features of the catheter and method of applying microwave energy a temperature profile can be predicted and produced that is similar to the temperature profile desired for the particular patient.

7 Claims, 4 Drawing Sheets

| | FREQ KHZ | TIME SECONDS | DEPTH | | | | | | | | | | | | | TEMP °C |
|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | |
| EXAMPLE 1 | 918 | 120 | 38 | 51 | 56 | 57 | 56 | 55 | 53 | 51 | 49 | 47 | 46 | 44 | 43 | |
| EXAMPLE 2 | 918 | 180 | 38 | 51 | 57 | 58 | 58 | 57 | 55 | 53 | 51 | 49 | 48 | 46 | 45 | |
| EXAMPLE 3 | 450 | 120 | 38 | 50 | 55 | 56 | 54 | 54 | 53 | 51 | 49 | 47 | 46 | 44 | 43 | |

METHOD OF CONSTRUCTING A MICROWAVE ANTENNA

This application is a division of application Ser. No. 09/511,961, filed Feb. 23, 2000 This application is a continuation-in-part of Ser. No. 08/641,045 U.S. Pat. No. 5,904,709, filed Apr. 17, 1996 and issued May 18, 1999, and is a continuation-in-part of U.S. patent application Ser. Nos. 09/162,457 now abandoned and 09/154,622 each filed Sep. 16, 1998, now U.S. Pat. No. 6,175,768 and is a continuation-in-part of U.S. Application Ser. No. 09/154,989 filed Sep. 17, 1998 now U.S. Pat. No. 6,134,476. +gi

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The present invention relates to apparatus, methods, and computer simulations highly suitable for treatment of benign prostatic hyperplasia (BPH) and, more particularly, to a unique catheter for microwave treatment of BPH to necrose prostatic tissue while protecting urethral tissue and computer simulations relating to the same.

2. Description of Prior Art

Benign prostatic hypertrophy or hyperplasia (BPH) is one of the most common medical problems experienced by men over 50 years old. Urinary tract obstruction due to prostatic hyperplasia has been recognized since the earliest days of medicine. Hyperplastic enlargement of the prostate gland, or enlargement due to abnormal but benign multiplication of the cells thereof, often leads to compression of the urethra thereby resulting in obstruction of the urinary tract. Common symptoms that develop from this condition may include more frequent urination, decrease in urinary flow, nocturia, pain, and discomfort. The incidence of BPH in men over 50 years of age is approximately 50 percent and increases to over 75 percent in men over 80 years of age. Symptoms of urinary obstruction occur most frequently between the ages of 65 and 70 when approximately 65 percent of men in the age group have prostatic enlargement.

When treatment by drug therapy is not sufficiently effective, surgical procedures for treating BPH are available but have potential side effects. General surgical risks apply such as anesthesia related morbidity, hemorrhage, coagulopathies, pulmonary emboli, electrolyte imbalance, and the like. Other problems that may occur from surgical correction include cardiac complications, bladder perforation, incontinence, infection, urethral or bladder neck stricture, retention of prostatic chips, and infertility. Due to the problems of surgery, many or even most patients delay treatment. However, the delay of treatment may lead to other complications including obstructive lesion in the prostate, chronic infection, and the like. Therefore it is unquestionable that a need exists for improved surgical or non-surgical methods for treating BPH.

Microwaves and other techniques have been used to necrose malignant, benign, and other types of cells and tissues including glandular and stromal nodules characteristic of benign prostate hyperplasia. However, problems encountered include a lack of focusing or direction of the energy thereby resulting in damage of healthy tissue.

The following patents disclose attempts to solve the above discussed difficult problems and related problems.

U.S. Pat. No. 5,904,709, issued May 18, 1999, to Arndt et al., and incorporated herein, discloses a method and apparatus for propagating microwave energy into heart tissues to produce a desired temperature profile therein at tissue depths sufficient for thermally ablating arrhythmogenic cardiac tissue to treat ventricular tachycardia and other arrhythmias while preventing excessive heating of surrounding tissues, organs, and blood. A wide bandwidth double-disk antenna is effective for this purpose over a bandwidth of about six gigahertz. A computer simulation provides initial screening capabilities for an antenna such frequency, power level, and power application duration. The simulation also allows optimization of techniques for specific patients or conditions. In operation, microwave energy between about 1 Gigahertz and 12 Gigahertz is applied to the monopole microwave radiator having a surface wave limiter. A test setup provides physical testing of microwave radiators to determine the temperature profile created in actual heart tissue or ersatz heart tissue. Saline solution pumped over the heart tissue with a peristaltic pump simulates blood flow. Optical temperature sensors disposed at various tissue depths within the heart tissue detect the temperature profile without creating any electromagnetic interference. The method may be used to produce a desired temperature profile in other body tissues reachable by catheter such as tumors and the like.

U.S. Pat. No. 5,843,144, issued Dec. 1, 1998, to Rudie et al., discloses a method for treating an individual with diseased prostatic tissue, such as benign prostatic hyperplasia, including inserting a catheter into a urethra to position a microwave antenna located within the catheter adjacent a prostatic region of the urethra. A microwave antenna is then driven within a power range for applying microwave energy substantially continuously to prostatic tissue to heat the prostatic tissue surrounding the microwave antenna at a temperature and for a time period sufficient to cause necrosis of the prostatic tissue.

U.S. Pat. No. 5,843,026, issued Dec. 1, 1998, to Edwards et al., discloses a method and apparatus for delivering controlled heat to perform ablation to treat the benign prosthetic hypertrophy or hyperplasia (BPH). According to the method and the apparatus, the energy is transferred directly into the tissue mass which is to be treated in such a manner as to provide tissue ablation without damage to surrounding tissues. Automatic shut-off occurs when any one of a number of surrounding areas to include the urethra or surrounding mass or the adjacent organs exceed predetermined safe temperature limits. The constant application of the radio frequency energy over a maintained determined time provides a safe procedure which avoids electrosurgical and other invasive operations while providing fast relief to BPH with a short recovery time. The procedure may be accomplished in a doctor's office without the need for hospitalization or surgery.

U.S. Pat. No. 5,830,179, issued Nov. 3, 1998, to Mikus et al., discloses a stent system and method for use in the prostate gland. The stent is made of a shape memory alloy such as nitinol, and has a low temperature martensite state, with a martensite transition temperature below body temperature, and a high temperature austenite state, with an austenite transition temperature at or above body temperature, and a memorized shape in the high temperature austenite state which is a helical coil of diameter large enough to hold the prostatic urethra open. The stent is used to heat the prostate and is left in the prostatic urethra while the prostate heals. After the prostate is substantially healed, the stent is cooled to its martensite state and is easily removed from the urethra.

U.S. Pat. No. 5,800,486, issued Sep. 1, 1998, to Thome et al., discloses an intraurethral catheter which includes a microwave antenna and a cooling lumen structure substantially surrounding the antenna. A cooling balloon partially surrounds the cooling lumens on one side of the catheter adjacent the microwave antenna. The cooling balloon improves wall contact between the catheter and a wall of the urethra to improve cooling of the urethra. The cooling balloon communicates with the cooling lumen structure to permit circulation of cooling fluid through the cooling balloon.

U.S. Pat. No. 5,800,378, issued Sep. 1, 1998, to Edwards et al., discloses a medical probe device comprising a catheter having a stylet guide housing with one or more stylet ports in a side wall thereof and a stylet guide for directing a flexible stylet outward through the stylet port and through intervening tissue at a preselected, adjustable angle to a target tissue. The total catheter assembly includes a stylet guide lumen communicating with the stylet port and a stylet positioned in said stylet guide lumen for longitudinal movement from the port through intervening tissue to target tissue. The stylet can be an electrical conductor enclosed within a non-conductive layer, the electrical conductor being a radio frequency electrode. Preferably, the non-conductive layer is a sleeve which is axially moveable on the electrical conductor to expose a selected portion of the electrical conductor surface in the target tissue. The stylet can also be a microwave antenna. The catheter can include one or more inflatable balloons located adjacent to the stylet port for anchoring the catheter or dilation. Ultrasound transponders and temperature sensors can be attached to the probe end and/or stylet. The stylet guide can define a stylet path from an axial orientation in the catheter through a curved portion to a lateral orientation at the stylet port.

U.S. Pat. No. 5,755,754, issued May 26, 1998, to Rudie et al., discloses an intraurethral, Foley-type catheter shaft containing a microwave antenna capable of generating a cylindrically symmetrical thermal pattern, within which temperatures are capable of exceeding 45° C. The antenna, which is positioned within the shaft, is surrounded by means within the shaft for absorbing thermal energy conducted by the tissue and asymmetrically absorbing electromagnetic energy emitted by the antenna—a greater amount of electromagnetic energy being absorbed on one side of the shaft. This asymmetrical absorption alters the thermal pattern generated by the microwave antenna, making it cylindrically asymmetrical, which effectively focuses microwave thermal therapy toward undesirous benign tumorous tissue growth of a prostate anterior and lateral to the urethra, and away from healthy tissue posterior to the urethra.

U.S. Pat. No. 5,733,315, issued Mar. 31, 1998, to Burdette et al., discloses an apparatus for applying thermal therapy to a prostate gland, comprising a support tube having a longitudinal central passageway, a power lead channeled through the longitudinal central passageway and an ultrasound crystal disposed around at least part of the support tube. The ultrasound crystal is coupled to the power lead which provides the power to energize the ultrasound crystal and generate ultrasound energy providing thermal therapy to the prostate gland. The ultrasound crystal further includes inactivated portions for reducing ultrasound energy directed to the rectal wall of the patient. A sealant is disposed in contact with the ultrasound crystal allowing vibration necessary for efficient ultrasound energy radiation for the thermal therapy to the prostate gland.

U.S. Pat. No. 5,720,718, issued Feb. 24, 1998, to Rosen et al., discloses a medical probe device comprising a catheter having a stylet guide housing with at least one stylet port in a side thereof and stylet guide means for directing a flexible stylet outward through at least one stylet port and through intervening tissue to targeted tissue. The stylet comprises an electrical central conductor which is enclosed within an insulating or dielectric sleeve surrounded by a conductive layer terminated by an antenna to selectively deliver microwave or radio frequency energy to target tissue. One embodiment includes the electrical conductor being enclosed within a non-conductive sleeve which itself is enclosed within a conductive sleeve in a coaxial cable arrangement to form a microwave transmission line terminated by an antenna. Another embodiment includes a resistive element near the distal end of the stylet which couples the center electrode to an outer conductor to generate joulian heat as electromagnetic energy is applied, such as an RF signal.

U.S. Pat. No. 5,643,335, issued Jul. 1, 1997, to Reid et al., discloses a system for treatment of benign prostatic hyperplasia within intraprostatic tissue surrounding a urethra. The system includes an intraurethral catheter having an intraurethral catheter shaft. An antenna is located within the catheter shaft for delivering heat to the intraprostatic tissue surrounding the urethra. Coolant fluid is circulated through a chamber located between the catheter shaft and the urethral wall.

U.S. Pat. No. 5,620,480, issued Apr. 15, 1997, to Eric N. Rudie, discloses a method for treating an individual with benign prostate hyperplasia. The method includes inserting a catheter into a urethra so as to position an energy emitting element located within the catheter adjacent a prostatic region of the urethra. A fluid is circulated within the catheter until the fluid stabilizes at a prechilled temperature. An energy emitting element is then energized sufficient to heat prostatic tissue surrounding the energy emitting element.

U.S. Pat. No. 5,599,294, issued Feb. 4, 1997, to Edwards et al., discloses a medical probe device comprising a catheter having a stylet guide housing with one or more stylet ports in a side wall thereof and guide means for directing a flexible stylet outward through the stylet port and through intervening tissue at a preselected, adjustable angle to a target tissue. The stylet can be an electrical conductor enclosed within a non-conductive layer, the electrical conductor being a radio frequency electrode. Preferably, the non-conductive layer is a sleeve which is axially moveable on the electrical conductor to expose a selected portion of the electrical conductor surface in the target tissue. The stylet can also be a microwave antenna.

U.S. Pat. No. 5,575,811, issued Nov. 19, 1996, to Reid et al., discloses a system for treatment of benign prostatic hyperplasia within intraprostatic tissue surrounding a urethra. The system includes an intraurethral catheter having an intraurethral catheter shaft. An antenna is located within the catheter shaft for delivering heat to the intraprostatic tissue surrounding the urethra. Coolant fluid is circulated through a chamber located between the catheter shaft and the urethral wall.

U.S. Pat. No. 5,509,929, issued Apr. 23, 1996, to Hascoet et al., discloses a urethral probe having a front part and a rear part, and a microwave antenna connected to an external device for generating microwaves. The microwave antenna has its primary active heating part arranged in the urethral probe to be directed onto the prostatic tissue located at least at the level of the bladder neck in the working position. The urethral probe constitutes an essential element of a device for the therapeutic treatment of tissues by thermotherapy, more particularly tissues of the bladder of a human being.

U.S. Pat. No. 5,464,437, issued Nov. 7, 1995, to Reid et al., discloses a system for treatment of benign prostatic hyperplasia within intraprostatic tissue surrounding a urethra. The system includes an intraurethral catheter having an intraurethral catheter shaft. An antenna is located within the catheter shaft for delivering heat to the intraprostatic tissue surrounding the urethra. Coolant fluid is circulated through a chamber located between the catheter shaft and the urethral wall.

U.S. Pat. No. 5,413,588, issued May 9, 1995, to Rudie et al., discloses an intraurethral, Foley-type catheter shaft containing a microwave antenna capable of generating a cylindrically symmetrical thermal pattern, within which temperatures are capable of exceeding 45° C. The antenna, which is positioned within the shaft, is surrounded by means within the shaft for absorbing thermal energy conducted by the tissue and asymmetrically absorbing electromagnetic energy emitted by the antenna—a greater amount of electromagnetic energy being absorbed on one side of the shaft. This asymmetrical absorption alters the thermal pattern generated by the microwave antenna, making it cylindrically asymmetrical, which effectively focuses microwave thermal therapy toward undesirous benign tumorous tissue growth of a prostate anterior and lateral to the urethra, and away from healthy tissue posterior to the urethra.

U.S. Pat. No. 5,366,490, issued Nov. 22, 1994, to Edwards et al., discloses a medical probe device comprising a catheter having a stylet guide housing with one or more stylet ports in a side wall thereof and guide means for directing a flexible stylet outward through the stylet port and through intervening tissue at a preselected, adjustable angle to a target tissue. The stylet can also be a microwave antenna.

U.S. Pat. No. 5,312,392, issued May 17, 1994, to Hofstetter et al., discloses a method of treating benign prostatic hyperplasia employing the steps of inserting a diffusing light guide into a prostrate lobe and providing laser power to the diffusing light guide in order to necrose surrounding tissue. The diffusing light guide can be inserted into the central or lateral prostrate lobes by inserting a needle and a trocar transperineally into the middle of the lateral lobe, removing the trocar, inserting the diffusing light guide, and monitoring the position of the needle, trocar, and diffusing light guide using ultrasound. The diffusing light guide can also be inserted into the central or lateral prostrate lobes transurethrally and positioned with the aid of an urethroscope.

U.S. Pat. No. 4,967,765, issued Nov. 6, 1990, to Turner et al., discloses a urethral inserted applicator for prostate hyperthermia including a multi-tube, balloon type catheter. The catheter includes first and second closed end fluid dry tubes, respectively, for a helical coil antenna type applicator, and a microwave type temperature sensor for measuring the temperature of the prostate tissue, and an open fluid receiving tube. A microwave generator supplies electromagnetic energy to the applicator. A comparator is connected to the temperature sensor and a temperature reference potentiometer for comparing the actual tissue temperature level with a desired temperature level and outputting control signals to the microwave generator for controlling the output to the applicator. The coil type applicator is an elongated coil having a tip end connected to the center conductor of a coaxial cable and an opposite end connected to the outer conductor of the coaxial cable. A sheet or sheath of insulation material covers the coil antenna for insulating the coil from the tissue and the thickness of the sheet may be varied to provide uniform tissue heating along the length of the coil. The balloon of the catheter engages the body's bladder to position the applicator properly during the treatment.

The above cited prior art does not provide an easily fabricated catheter that may be fabricated with variations useful for individual patients, a computer simulation to predict the effect of procedural techniques, and a relatively quick procedure that may be performed in minutes to necrose prostatic tissue while protecting healthy tissue. Consequently, there is a strong need for improved treatment techniques that accurately pinpoint and necrose selected prostatic tissue while protecting the urethra and other healthy structures by cooling and by selectively directing microwave radiation. Those skilled in the art have long sought and will appreciate the present invention that addresses these and other problems.

SUMMARY OF THE INVENTION

The present invention provides a procedure, apparatus, and computer simulation for treating benign prostatic hyperplasia (BPH). The computer simulation may be used to predict a temperature profile that will be produced given the various inputs related thereto. Alternatively, it may be used to provide suitable procedure variables such as frequency, time duration, and power level, given the desired temperature profile. The procedure has a treatment time of only a few minutes and is designed to prevent damage to healthy tissue such as the urethra. The antenna may be made directional to protect structures such as the colon and structures such as ducts radially outside the urethra. For purposes of the present invention, a catheter is assumed to include a probe, cannula or other medical device for insertion into the body such as into the urethra for treatment purposes.

For this purpose, a transcatheter microwave antenna is disclosed that comprises a catheter preferably formed from a microwave transmission line having first and second opposing ends. The first end may be adapted for connection to a microwave power source. The microwave transmission line preferably has a center conductor and an outer conductor. A microwave antenna is disposed on the second end of the microwave antenna. A layer of fusion material is disposed radially outward of the microwave antenna. The fusion material is operable to be in a first physical state prior to operation of the microwave antenna. The fusion material is alterable to a second physical state from the first physical state to provide heat of fusion cooling adjacent the catheter during operation of the microwave antenna. In a preferred embodiment, the fusion material may be in a solid physical state prior to operation of the microwave antenna and is operable for melting to a liquid state during operation of the microwave antenna so as to provide cooling radially outward from the catheter. The fusion material in the solid state is substantially flexible. The fusion material is substantially transparent to microwave radiation so as to absorb little energy directly from the microwave radiation. In one embodiment, the fusion material has a melting point in the range of from approximately eighty to one hundred degrees Fahrenheit.

Electrical insulating material is preferably provided between the center conductor and the outer conductor. The microwave antenna may be disposed within the electrical insulating material in a preferred embodiment. An outer sheath preferably but not necessarily surrounds the fusion material. The layer of fusion material is provided in surrounding relationship to the microwave antenna. In one embodiment, the fusion material is comprised of a crystalline material. In another embodiment, the fusion material is comprised of powdered material. The fusion material, in one embodiment, may be comprised of either dibasic sodium phosphate or phosphonium chloride.

Preferably a tubular conductor acts as an attenuator of microwaves and may be mounted at or near a surface of the catheter and may be axially positioned on the catheter adjacent the microwave antenna. In one embodiment of the invention, material is provided for absorbing microwave heat energy on one side of the microwave antenna so as to make the microwave antenna directional.

A method of constructing a transcatheter microwave antenna may include providing a coaxial cable with a center conductor and an outer conductor. The coaxial cable is adapted for connection to a microwave power source. A microwave antenna at one end of the coaxial cable and a layer of fusion material is provided adjacent the microwave antenna. The fusion material is operable to be in a first physical state prior to operation of the microwave antenna and may be alterable to a second physical state from the first physical state to provide heat of fusion cooling adjacent the catheter during operation of the microwave antenna. The fusion material is selected to have a melting temperature in the range from about eighty to one hundred degrees Fahrenheit.

A method for selective thermal necrosing of a tissue to be treated while limiting thermal damage to a protected tissue that comprises positioning an energy radiator adjacent to heat the tissue to be treated such that the protected tissue is between the tissue to be treated and the energy radiator. A layer of fusion material is positioned between the energy radiator and the protected tissue such that convection transfer of energy may occur between the protected tissue and the layer of fusion material. Energy is radiated from the energy radiator to heat the tissue to be treated. The temperature rise in the protected tissue is limited by convection transfer of energy between the protected tissue and the fusion material. The temperature rise in the fusion material is limited by changing the fusion material from a first physical state to a second physical state due to the convection transfer of energy between the protected tissue and the fusion material. The fusion material preferably has a melting point below body temperature. The energy radiator may be controlled so as to direct energy from the energy radiator in one or more selected directions toward the tissue to be treated. This may be accomplished by positioning the energy absorbing material adjacent the energy radiator to absorb energy from the energy radiator. A frequency of operation may be selected based on a distance of the energy radiator to the tissue to be treated so as to focus energy to the tissue to be treated.

Thus, in operation a method for selective thermal ablation of a tissue to be treated is provided that limits thermal damage to protected tissues and comprises positioning fusion material adjacent the protected tissue to permit convection transfer of energy between the fusion material and the protected tissue, the fusion material preferably has a melting point lower than body temperature. Energy is radiated through the fusion material and through the protected tissue and into the tissue to be treated. Microwaves along the outside of the catheter are attenuated with a tubular conductor. The microwave antenna may be adjusted so that the radiation points deposit energy at a selected distance of the tissue to be treated from the microwave antenna.

A computer program is provided for simulating treatment in biological tissue which comprises providing at least one antenna characteristic for the microwave antenna. At least one tissue characteristic is provided of the tissue into which microwave energy is to be deposited. At least one cooling characteristic of cooling substances through which microwaves are transmitted is provided. A frequency of operation and a power level may be provided. A delivery time for the microwave energy may be provided. A temperature profile produced within the biological tissue may be determined. The temperature versus distance radially outward from the microwave antenna may be displayed graphically in some manner. The changes in the temperature profile with time may be displayed. The computer program may also include a characteristic of absorption material for absorbing the microwave energy in at least one direction so as to alter the temperature profile accordingly.

One object of the present invention is to provide an improved instrument and method for necrosing certain tissue while protecting other tissue.

Another object of the present invention is to provide an improved instrument, method, and computer simulation for treating benign prostatic hyperplasia.

Yet another objective of the present invention is to provide a treatment that necroses prostatic tissue but protects other tissue such as the urethra.

Any listed objects, features, and advantages are not intended to limit the invention or claims in any conceivable manner but are intended merely to be informative of some of the objects, features, and advantages of the present invention. In fact, these and yet other objects, features, and advantages of the present invention will become apparent from the drawings, the descriptions given herein, and the appended claims.

While the present invention will be described in connection with presently preferred embodiments, it will be understood that it is not intended to limit the invention to those embodiments. On the contrary, it is intended to cover all alternatives, modifications, and equivalents included within the spirit of the invention and as defined in the appended claims.

BRIEF DESCRIPTION OF PREFERRED EMBODIMENTS

The techniques, catheter, and computer simulation of the present invention have the goal of achieving deep heating of tissue without overly heating tissue directly surrounding the catheter as is particularly useful for treating benign prostatic hyperplasia without damaging the urethra. A small, highly efficient antenna delivers microwave power radiation within a field of the necessary size and volume to necrose tissue. The catheter also contains a cooling means to control surface temperature and shallow depth heating. This application incorporates herein by reference U.S. Pat. No. 5,904,709, filed Apr. 17, 1996 and issued May 18, 1999, U.S. patent application Ser. Nos. 09/162,457 and 09/154,622 each filed Sep. 16, 1998, and U.S. application Ser. No. 09/154,989 filed Sep. 17, 1998.

Figure 1:
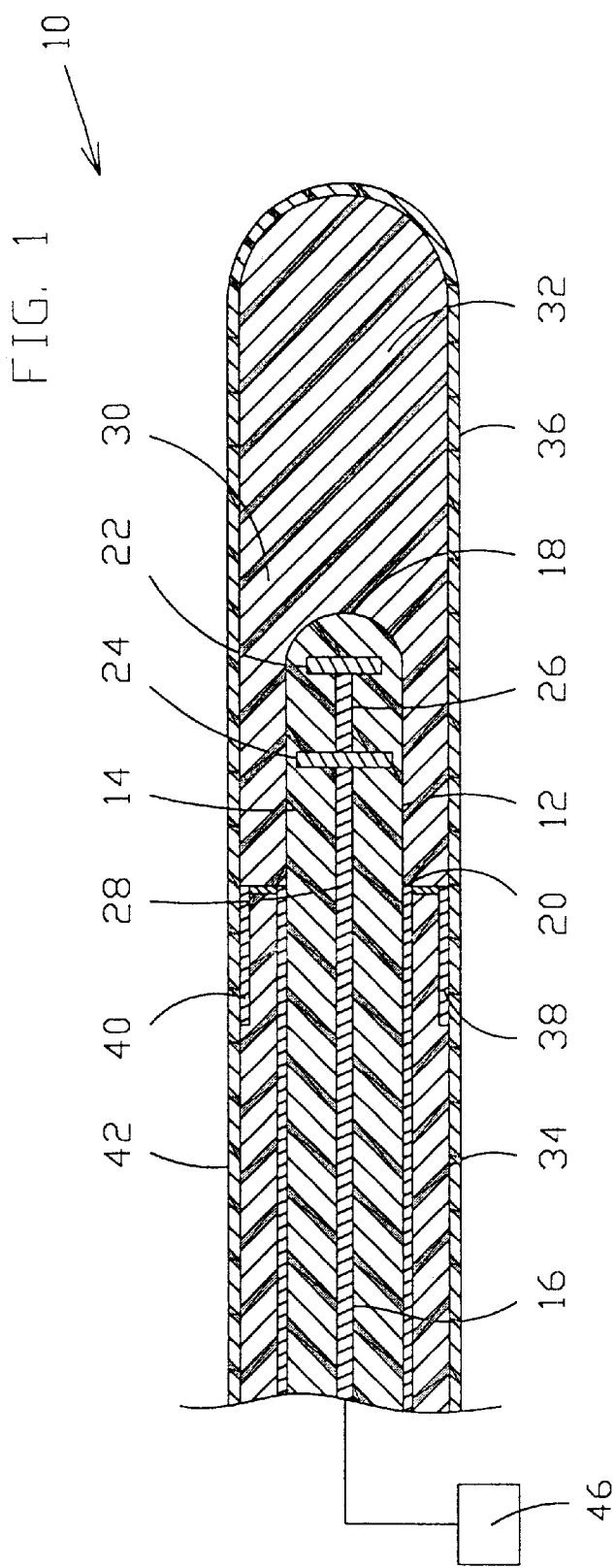
FIG. 1 is an elevational view, in section, of a catheter with a microwave antenna surrounded by a layer of fusion material that cools surrounding tissue through heat of fusion.

Referring now to the drawings, and more particularly to FIG. 1, the present invention discloses catheter 10 with microwave antenna 12 in accord with the present invention. Although variations for a microwave antenna to be used with catheter 10 are possible, microwave antenna 12 is a presently preferred embodiment of the invention. Microwave antenna 12 includes body 14 made of insulating material such as TEFLON. Microwave antenna 12 may be made from a standard coaxial cable having a center conductor 16 and sheath 20. Because of the small diameter, microwave antenna 12 is especially useful for a catheter. The diameter of microwave antenna 12 may be in the range of about 2 millimeters. Radiation from antenna 12 is directed substantially orthogonally to antenna center conductor 16 or more specifically monopole 26 and is concentrated between end 18 and feed point 28 which is located at the end of sheath 20. In a homogenous environment, microwave antenna 12 is non-directional and radiates with radial symmetry. The double-disk monopole design includes tip disk 22 and tuning disk 24 mounted to pole 26 which is an extension of center conductor 16. This design has a very broad bandwidth so that it can be used over a wide range of frequencies with little degradation in performance. Therefore, manufacturing and operating environment variations are well tolerated.

Radiation from antenna 12 occurs mainly from the discontinuities such as feed point 28, tip disk 22, and tune disk 24. Control of various features of the antenna may include adjustment of the axial spacings of the elements such as the axial spacing between feed point 28 and tip 18, between feed point 28 and tuning disk 24, and between tuning disk 24 and tip disk 22. Such adjustments alter the radiation pattern from antenna 12. Other changes that affect the radiation pattern include the diameter of the tuning disk 24 and tip disk 22. Control of these variables and others discussed in the parent to this application referenced above may be used to vary the radiation pattern and the resulting heating profile. Computer simulations discussed in the parent to this application and here subsequently allow manipulation of such variables to obtain the heating profile most similar to that desired.

For use in treatment of benign prostatic hyperplasia without damaging the urethra, it important to cool catheter 10 in order to save tissue, such as the urethra, immediately adjacent to catheter 10. If microwave heating is administered via the urethra, the present invention may be used to save the urethra while still thermally necrosing or ablating the enlarged prostatic tissue surrounding the urethra. Fusion material 30 disposed around antenna 12 is used to keep catheter 10 cool. Because catheter 10 is necessarily in immediate contact with the urethra, the urethral tissue will also remain cool. Fusion material 30 uses the heat of fusion to maintain the temperature at the melting point of fusion material 30. The energy required to change a solid to a liquid while remaining at the melting point temperature is well known as the heat of fusion of a material. When fusion material 30 is heated, its temperature rises until reaching the melting point. At the melting point, the temperature remains constant until all of the fusion material has melted. Depending on the type of fusion material used, the urethral tissue may remain substantially at body temperature assuming the melting point of fusion material 30 is at or near body temperature. To increase the volume of fusion material involved, it is generally desirable to have a compartment of fusion material in catheter 10 not only surrounding antenna 12 but also forward of antenna 12 in region 32 and behind antenna 12 in region 34. Fusion material is held in position by sheath 36 although conceivably if fusion material 30 is completely harmless to the body, and if desired, sheath 36 could be left off. Another use of sheath 36 is to maintain a certain size catheter such that attenuator 38, which is a tubular conductor, may be used to reduce microwave current flowing back along the outside surface of catheter 10. Attenuator 38 is preferably positioned such that it is at or near the surface of catheter 10. In the present embodiment, attenuator 38 has a surface 40 positioned just below surface 42 of catheter 10. Attenuator 38 is preferably electrically connected to sheath 20.

When catheter 10 transmits microwaves in the urethra and the temperature of fusion material 30 reaches the melting point, then fusion material 30 begins to change from one physical state, the solid state, to a second physical state, the liquid state. While changing states or melting, fusion material 30 removes heat from surrounding tissue due to microwave radiation. This process continues until all of fusion material 30 has changed to the liquid state. Materials exist that are highly effective for cooling purposes due to having a high heat of fusion. More heat can be removed if the material selected for fusion material 30 has a high heat of fusion. This makes possible a longer heating time, if desired. As examples only, two substances that have desirable properties for use in the present application include dibasic sodium phosphate and phosphonium chloride. Other materials could also conceivably be used.

Fusion material 30 should preferably have a melting point at about body temperature or below. A range of presently preferred melting points is from about 90° F. to 100° F. In some cases, to effect cooling over a greater radius from catheter 10, it might be desirable to use fusion material with lower melting points. A fairly wide range of values for the melting point well outside of the above range may be used depending on the volume of tissue to be protected or, in other words, depending on the desired temperature profile for tissue heating. However, in the computer simulations discussed subsequently, it is assumed that the melting point is at body temperature.

In addition, fusion material 30 should be sufficiently flexible that it will easily track the path of the urethra. It may be desirable to provide fusion material 30 in a crystalline, granular, or powder form to provide sufficient flexibility while fusion material 30 is in the solid state.

Another criteria for fusion material 30 is that it is microwave transparent or nearly so. Generally powders and crystals as may be used for flexibility also tend to absorb little or no microwave energy so as to be microwave transparent. This feature is desirable so that only the heat energy convexly flowing from the urethra is used to melt fusion material 30 rather than the microwave energy directly received from antenna 12.

If it is desired to re-use catheter 10, then there is an additional requirement that when the material is resolidified, that it is possible to insure that fusion material 30 will return to the powder or granular form so that catheter 10 remains flexible. It may be necessary to ultrasonically powderize the resolidified material or otherwise act on it to effect this purpose. However, due to the simplicity of construction of catheter 10 and the very low cost if produced in quantity, catheter 10 may simply be discarded after use.

Due to the simple construction, catheter 10 may be inexpensively produced with different antenna spacings for different widths and depths of regions to be heated. The diameter of catheter 10 may vary between a very approximate range of from about 3 millimeters to about 7 millimeters depending on urethra size and blockage. The diameter may also be considered in determining the desired heating time. The volume of the catheter increases with the square of the radius so that even a slight increase in radius of catheter 10 significantly increases potential cooling power.

In some cases, it may be desirable to apply microwave heating via the colon. The heat of fusion type of cooling discussed above is also effective to protect the colon. Generally, significantly more fusion material 30 can be used when applying heat through the colon due to the possibility of using a larger catheter. Thus, heating through the colon provides the possibility of a much longer heating time if that is desired. As well, when heating through the colon, a modified version catheter 10A is preferably used as indicated in FIG. 7 so that antenna 12 is effectively directional and colon tissue is not unnecessarily heated.

Figure 7:
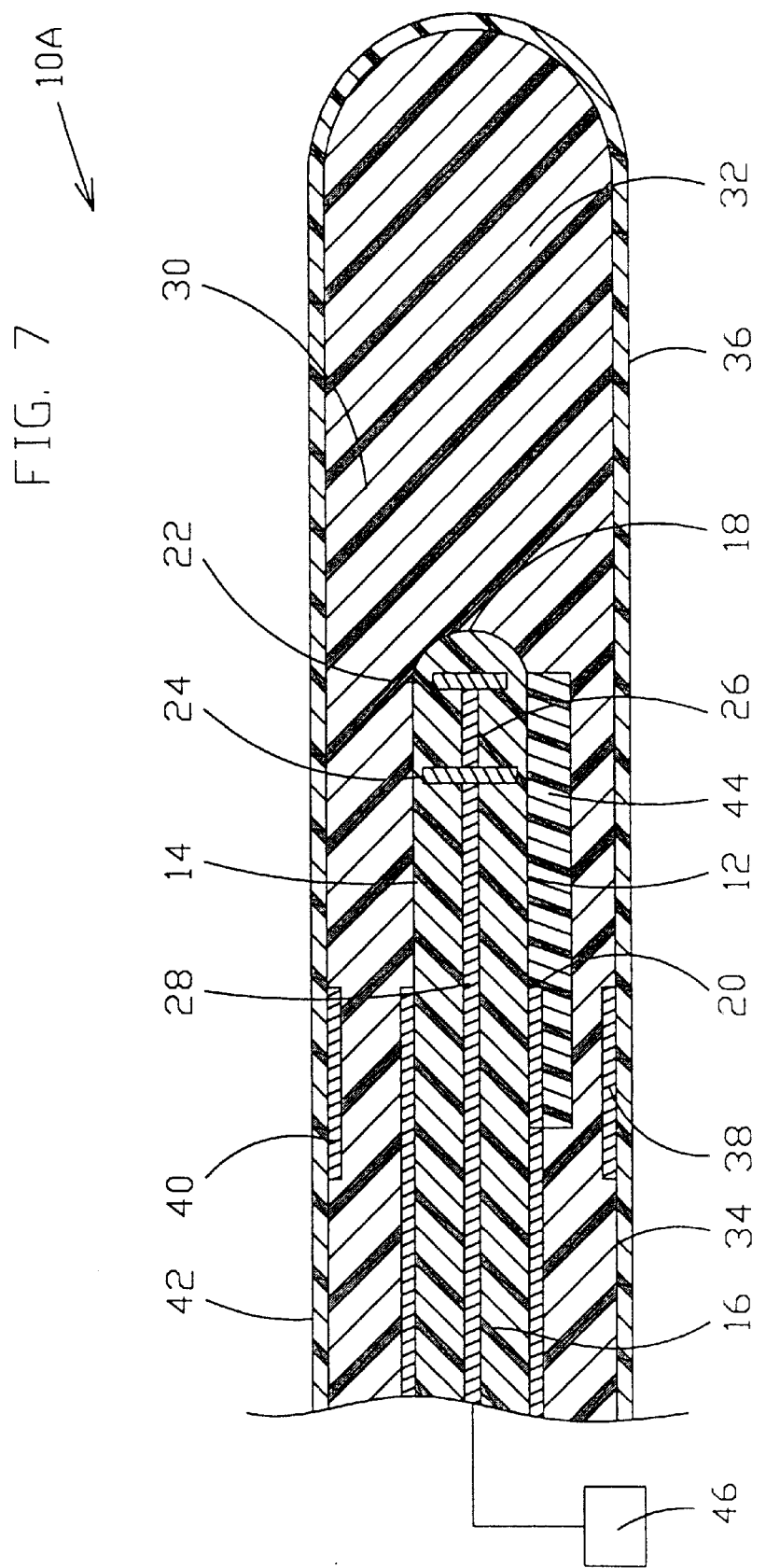
FIG. 7 is an elevational view, in section, of a catheter with a microwave antenna surrounded by a layer of material that cools surrounding tissue through heat of fusion along with a energy absorption layer for absorbing microwave energy so that the microwave antenna is directional.

A preferred technique for making antenna 12 directional is to include microwave absorbing material 44 within the enlarged catheter 10A as indicated in FIG. 7. Microwave absorbing material 44 is not transparent to microwave radiation but instead readily absorbs microwave radiation to substantially limit transmission in undesired directions such as any direction except toward the prostrate tissue. This technique tends to be much simpler than using directional elements in the antenna, although directional elements could also be used. The substantially increased amount of fusion material 30 in catheter 10A will offset the heat generated within absorbing material 44. Also, since there is some distance to the prostate region to be heated, the significant radiation points 22, 24, and 28 may be moved further apart and phased to provide focusing at some selected depth.

It may also be desirable in certain circumstances to use a thin strip of absorbing material, such as absorbing material 44, in catheter 10 for use in the urethra to thereby reduce radiation in a particular direction, e.g., such as in the particular direction of the ejaculatory duct and the like that may be positioned outside the region of protection provided by fusion material 30. In this manner, catheter 10 for use in the urethra may be made directional if desired.

Thus, there are many possibilities for control of the temperature profile to be produced. The relatively simple construction of catheter 10 or 10A and the materials are of relatively very low cost as compared to other catheters, so that numerous variations may be made and perhaps individually designed catheters may be used without significantly increased capital investment. It will be understood that operating and power control equipment 46 may be used at the end of catheter 10 for controlling radiating power for catheter 10.

Figure 2:
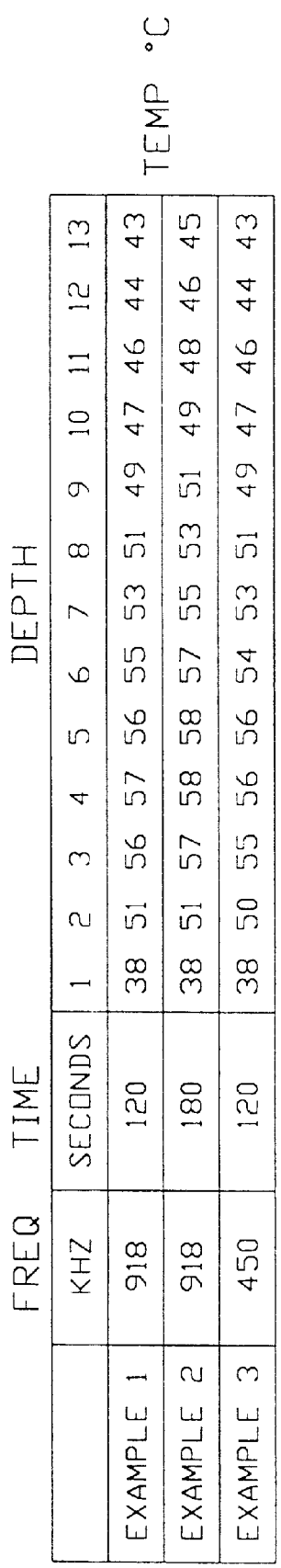
FIG. 2 is a table showing computer simulation results with temperature versus depth for a catheter in accord with the present invention.

FIG. 2 shows several temperature versus depth computer projections for use of catheter 10. For purpose of the simulation, it is presumed that the melting temperature of fusion material 30 is body temperature or 38° C. As can be seen in Example 1, which is also displayed three dimensionally in FIG. 3, the temperature in tissue surrounding catheter 10 is heated such that in the range of from two to nine millimeters from the catheter significant necrosing of tissue will occur. An advantage is that the heating time is only two minutes so that the treatment is fairly quick. The power level is 3 watts. The volume of tissue heated over ten degrees centigrade is 807 cubic millimeters. Significant amounts of tissue may be necrosed when tissue temperature is raised by about ten degrees. The likelihood of tissue ablation is related largely to the maximum temperature and the time duration of heating. The total amount of energy deposited or the amount of energy deposited in any layer can be displayed as desired. Note that the urethra temperature would remain cool, but heating beyond the urethra is adequate to necrose cells out to a distance of approximately one centimeter. If deeper heating is needed, this can be obtained with longer delivery times and/or adjusting focusing, power level, and frequency of antenna 12. However, the delivery time is limited by the total fusion time of fusion material 30. When used though the colon, the heating time can be significantly increased due to having a greater amount of fusion material as discussed hereinbefore.

In Example 2, the frequency and the power level is the same as that of Example 1 but the heating time is three minutes. The volume of tissue ablated or necrosed will be increased as indicated by the higher temperatures but also by the increased time duration. The volume of tissue heated over ten degrees centigrade is 1295 cubic centimeters.

Example 3 shows the effect of changing the frequency to 450 kHz thereby resulting in another temperature profile. In Example 3, the power level is 3 watts and the heating time is two minutes. The volume of tissue with a temperature increase over ten degrees is 811 cubic millimeters. In Example 1 and 2, the conductivity is 0.95 mhos/meter and in Example 3, the conductivity is 0.83 mhos/meter.

Figure 3:
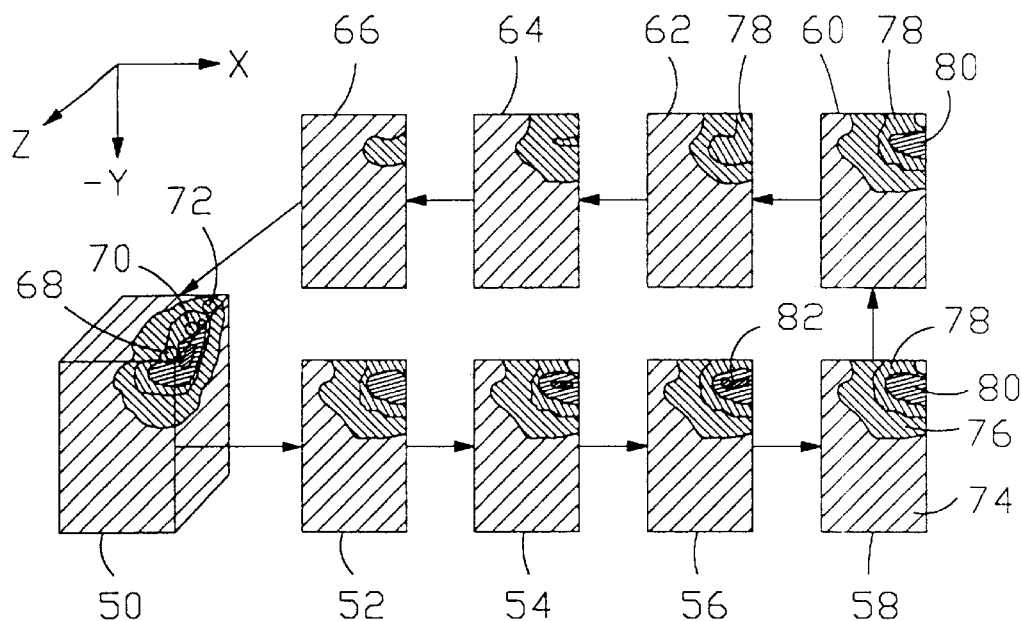
FIG. 3 is a three dimensional depiction of an isothermal profile produced with the catheter of FIG. 1 operating at 918 KHz for 120 seconds and other selected system parameters.
Figure 4:
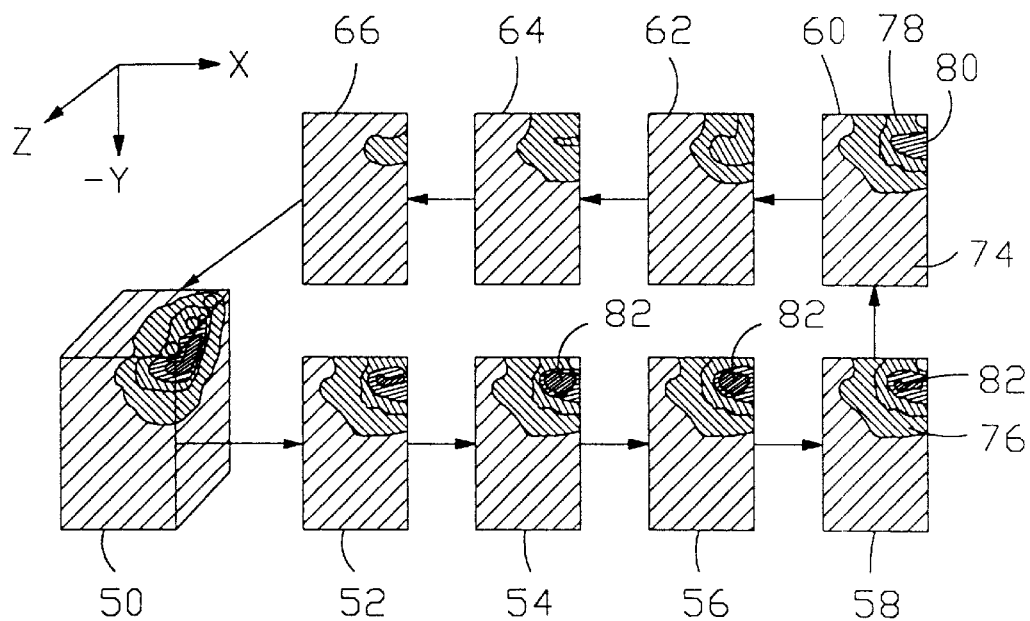
FIG. 4 is a three dimensional depiction of an isothermal profile produced with the catheter of FIG. 1 operating at 918 KHz for 180 seconds and other selected system parameters.
Figure 5:
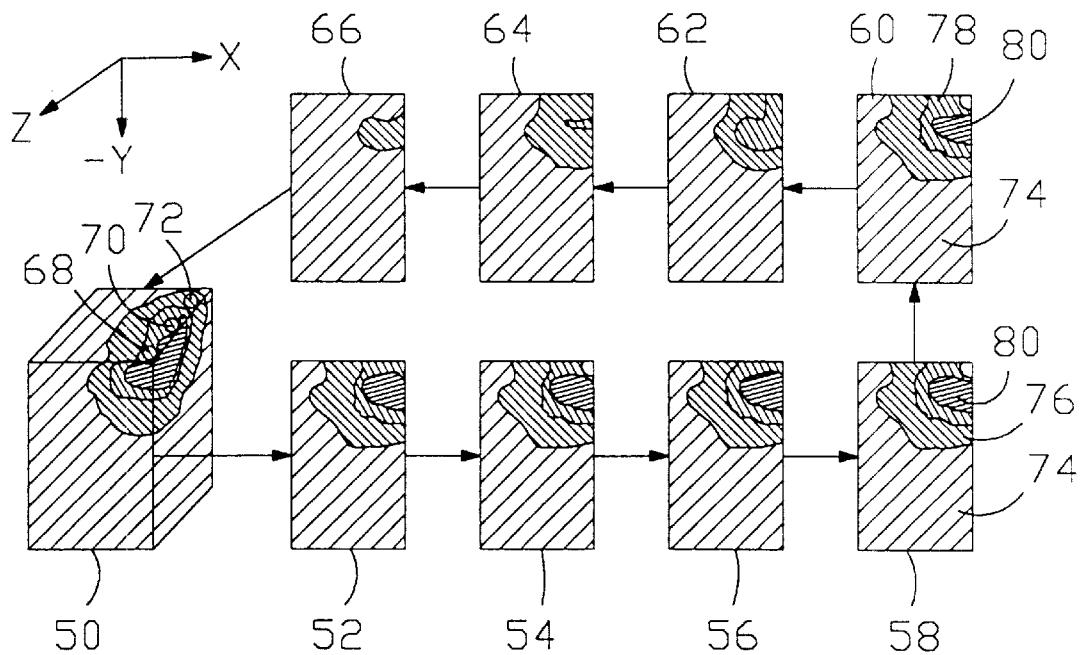
FIG. 5 is a three dimensional depiction of an isothermal profile produced with the catheter of FIG. 1 operating at 450 KHz for 120 seconds and other selected system parameters.

A different comparison can be obtained by reviewing the isothermal layers of temperature rather than a temperature change in a particular straight line out from catheter 10 as per the chart of FIG. 2. One method of reviewing the temperature is to provide several slices of a selected cube of simulated tissue surrounding catheter 10. In FIG. 3 through FIG. 5, cube 50 of tissue is one of four cubes surrounding catheter 10. For each variation of transmission characteristics, cube 50 is shown in each figure along with eight respective x-y cross-sections or slices starting from front of cube 50 and going towards the back of cube 50 as indicated by the view. Therefore, slice 52 is the front slice and the next seven slices 54, 56, 58, 60, 62, 64, and 66 show progressively deeper slices. The antenna is positioned such that discontinuities from which most radiation is broadcast are along the top edge of the selected portion of cube 50 with three discontinuities 68, 70, and 72 indicated by the circles. These discontinuities may be related to tip disk 22, tuning disk 24 and antenna feedpoint 28.

The isothermal zones of temperature are indicated by the respective types of shading although preferably a color diagram would be presented. For this example, the outermost thermal shading zone 74 represents tissue that is heated such that the temperature change is less than five degrees centigrade. Thermal shading zone 76 represents tissue that is heated such that the temperature change is more than five degrees centigrade but less than ten degrees centigrade. Thermal shading zone 78 represents tissue that is heated such that the temperature change is more than ten degrees centigrade but less than fifteen degrees centigrade. Thermal shading zone 80 represents tissue that is heated such that the temperature change is more than fifteen degrees centigrade but less than twenty degrees centigrade. Thermal shading zone 82 represents tissue that is heated such that the temperature change is more than twenty degrees centigrade.

The exact temperature at which tissue is ablated or necrosed will vary depending on various factors. The length of time the tissue remains at an elevated temperature and the maximum temperature are important factors. For relatively short periods of time, tissue heated above twenty degrees centigrade is highly likely to be necrosed. In FIG. 4, it can be seen that a significant or high percentage of the volume of tissue in thermal shading zone 82 will be necrosed due to higher temperature and also the longer heating time. Assuming the catheter is positioned at the location at which blockage of the urethra occurs, then it is anticipated that as the tissue dies and is reabsorbed by the body then relief may be obtained from the benign prostatic hyperplasia condition. Tissue in thermal shading zones 80 will also likely be necrosed. As well it is anticipated that at least a significant amount of tissue in shading thermal zone 78 will be necrosed. The effect of frequency and time changes can be seen by reviewing FIG. 3 through FIG. 5 where other factors such as cooling adjacent the catheter, power level, tissue characteristics, and antenna characteristics are kept constant. Further details concerning the various characteristics are discussed below and in the parent to this application.

Moreover, the tissue immediately surrounding the catheter out to about one millimeter is virtually unaffected by the heating. Thus, it is anticipated that a treatment would be relatively quick with fewer side effects than other microwave treatments presently used. It will be appreciated from the above that the temperature profile can be controlled to a great extent and so can made to match a desired pattern. Moreover, the expected response can be tested for numerous variations using the computer simulation of the present invention.

Figure 6:
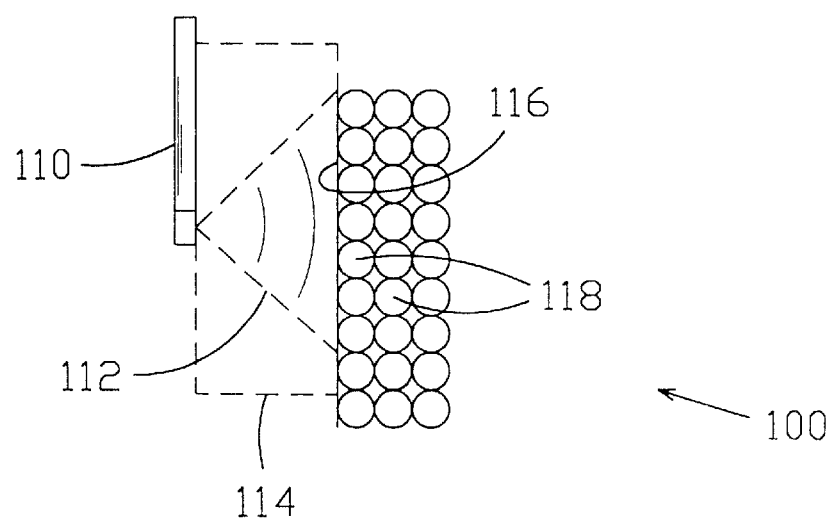
FIG. 6 is a schematic representation of a microwave thermal simulation model for simulated in-vivo operation of the catheter of FIG. 1.

FIG. 6 shows the general design of simulation elements for a microwave radiator system, such as computer simulated system 100. The computer simulation has been written to determine the temperature profiles that can be provided in the prostate tissue. The simulation is performed by an accordingly programmed computer in which the program may be stored within a storage medium such as a hard disk or diskette. The computer effectively acts as a simulator in accord with the programming that may be contained in a memory. The inputs to the program include antenna characteristics, tissue characteristics, the frequency, power level, and delivery time of the microwave energy. A temperature profile may be produced as discussed above that shows temperature versus distance radially or orthogonally outwardly from the catheter or antenna axis. Temperature variations may also be displayed over a selected period of time.

Simulated catheter antenna 110 generates microwave radiation that travels through various medium. Although the simulation of the present invention may be used for simulating microwave energy radiation into prostate tissue, it will be apparent that other uses are also available. The antenna will have various characteristics some of which are discussed in more detail in the parent to this application. In this embodiment, simulated fusion material 114 preferably forms an outer layer of catheter antenna 110 and represents the first medium through which the microwave energy must travel. As discussed above, simulated fusion material layer 114 is preferably transparent to microwave radiation. To maintain urethral cooling, fusion material 114 is in direct contact with tissue 116. For the outputs shown in FIG. 2 through FIG. 5, it was assumed that fusion material 114 had a melting point at body temperature. Microwave energy 112 emerges from catheter antenna 110 and travels unopposed through simulated fusion material 114 to engage simulated tissue 116. For a urethral catheter, fusion material 114 of catheter antenna 110 will necessarily be in held in direct contact with tissue 116 due to the relative size of catheter 10 and the urethra.

In the simulation, the microwave energy travels through tissue 116 and heats selected volume elements of simulated tissue referred to as computation cells 118. Each computation cell 118 is arbitrarily selected to be one or two cubic millimeters in size in the presently preferred embodiment of the simulation although this size may be varied. The energy applied to these cells by microwave radiation is determined for each selected time increment. As well, the computer computes the energy that leaves/arrives each computation cell 118 due to thermal conduction for each computation cell 118 for each selected time increment. In this manner, a computer simulation can determine the temperature profile for the tissue over a total desired heating duration. The total desired heating duration will typically consist of a plurality of short time increments.

The inputs to the simulation include, for instance, the conductivity and relative permittivity of the prostate tissues at higher frequencies. Conductivity is especially important since the conductivity primarily determines the rate of absorption of the microwave energy into the tissue and the maximum propagation distance through the tissue.

In a presently preferred embodiment of the simulation, a computational tissue cube having a size that correlates to a region of tissue to be ablated is given the electrical and thermal characteristics of in-vivo prostatic tissue. The cube is subdivided into 8000 small cubes with each cube being a computational cell such as computation cell 118. The instantaneous heat of one arbitrary computational cell in the cube is given by:

$$Q_C = Q_C^\circ + (\Delta Q_{RF} + \int \Delta Q_{HC})\Delta t$$

where:

Q is the new heat energy in the computational cell;

$Q_C^\circ$ is the previous heat energy level;

$\Delta Q_{RF}$ is the heat added due to absorption of microwave energy;

$\int \Delta Q_{HC}$ is the net heat added or lost by the cell from heat conduction; and $\Delta t$ is a small time constant.

The new temperature of the cell is given by:

$$T_C = Q_C/MS$$

where:

$T_C$ is the new cell temperature in °C.;

M is the mass of the cell; and

S is the specific heat of the cell.

Each cell is assumed to be a cube with six faces. The heat energy transferred through each face for one time increment is given by:

$$\Delta Q = -KA(\partial T/\partial r)\Delta t$$

where:

$\Delta Q$ is the heat transferred through one face;

K is the thermal conductivity of the cell;

$\partial T/\partial r$ is the temperature gradient from the center of one cube to the next; and A is the area of one face.

The electric field intensity in a cell is given by:

$$\hat{E}_1 = \frac{\hat{E}_{01} e^{-\gamma r_1}}{r_1^2}$$

where:
- $\hat{E}_1$ is the electric field intensity resulting from the radiation at the feed point of the antenna;
- $\hat{E}_{01}$ is related to the relative magnitude and phase of radiation from the feed point;
- $\gamma = \alpha + j\beta$;
- $\alpha$ is the attenuation constant associated with the tissue;
- $\beta$ is the phase shift constant; and
- $r_1$ is the distance from the antenna feed point to the center of a cell.

The total electric field at a cell due to radiation from the feed point, middle disk and top disk (each being a microwave radiator) is given by:

$$\hat{E} = \hat{E}_1 + \hat{E}_2 + \hat{E}_3$$

where:
- $\hat{E}_2$ is calculated similarly to $\hat{E}_1$ except using $r_2$ to the mid-disk; and
- $\hat{E}_3$ similarly using top disk associated $r_3$.

Finally, the energy absorption at the cell is given by:

$$W_a = v\sigma |E|^2 \Delta t$$

where:
- $W_a$ is the electromagnetic energy absorbed;
- v is the volume of the cube; and
- $\sigma$ is the conductivity of the medium.

The results from the simulation can be plotted in numerous ways such as those disclosed above. As well, given a particular desired profile the necessary input characteristics can be obtained such as power levels, operating time and frequency. Thus, the simulation can be used to determine results from particular inputs or to calculate the necessary inputs to obtain desired results.

In operation of the present invention, a computer simulation may be used to determine to predict what the temperature profile will be in the prostatic tissue. The temperature profile can be modified until it appears to fit the desired result. The amount of tissue to be necrosed can be calculated. The procedure goes fairly quickly. The heat of fusion material 30 should be in a solid state although flexible. The catheter is then positioned in the urethra at the desired position at which prostatic tissue is to be selectively removed. The microwave antenna is turned on at the predetermined power level for the predetermined heating time. The urethra is undamaged due to the heat of fusion material 30. In the next several weeks, the body reabsorbs necrosed tissue thereby providing relief to the patient of benign prostatic hyperplasia symptoms.

While the preferred embodiment of the catheter apparatus and methods are disclosed in accord with the law requiring disclosure of the presently preferred embodiment of the invention, other embodiments of the disclosed concepts may also be used. Therefore, the foregoing disclosure and description of the invention are illustrative and explanatory thereof, and various changes in the method steps and also the details of the apparatus may be made within the scope of the appended claims without departing from the spirit of the invention.

What is claimed is:

1. A method of constructing a transcatheter microwave antenna, comprising:

providing a cable with one or more conductors to form a catheter operable for insertion into the body;

adapting said cable for connection to a microwave power source;

providing a microwave antenna at one end of said cable;

providing a layer of microwave transparent fusion material in a first physical state adjacent said microwave antenna, said fusion material being alterable to a second physical state from said first physical state to provide heat of fusion cooling adjacent said catheter during operation of said microwave antenna.

2. The method of claim 1, further comprising:

selecting said microwave transparent fusion material to have a melting temperature in the range from about eighty to one hundred degrees Fahrenheit.

3. The method of claim 1, further comprising:

providing that said first physical state is a solid physical state, and selecting said microwave transparent fusion material in said solid physical state to be sufficiently flexible for use with said catheter such that said catheter is bendable within the body.

4. The method of claim 1, further comprising:

providing that said microwave transparent fusion material is in surrounding relationship to said microwave antenna.

5. The method of claim 1, further comprising:

providing that said microwave antenna is directional.

6. The method of claim 1, further comprising:

providing that said fusion material is a powdered substance when in said first physical state.

7. The method of claim 1, further comprising:

providing that said fusion material is a crystalline substance when in said first physical state.

* * * * *